United States Patent
Iwashita et al.

(10) Patent No.: US 9,643,993 B2
(45) Date of Patent: May 9, 2017

(54) CRYSTALLINE POLYMORPHIC FORM OF ULIPRISTAL ACETATE

(71) Applicant: ASKA PHARMACEUTICAL CO., LTD., Tokyo (JP)

(72) Inventors: Shigeki Iwashita, Kanagawa (JP); Hiroyuki Hayashi, Kanagawa (JP); Koichi Miyazaki, Kanagawa (JP)

(73) Assignee: Aska Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 14/431,351

(22) PCT Filed: Sep. 26, 2013

(86) PCT No.: PCT/JP2013/005709
§ 371 (c)(1),
(2) Date: Mar. 26, 2015

(87) PCT Pub. No.: WO2014/050106
PCT Pub. Date: Apr. 3, 2014

(65) Prior Publication Data
US 2015/0239927 A1 Aug. 27, 2015

(30) Foreign Application Priority Data

Sep. 28, 2012 (JP) ................................ 2012-215436

(51) Int. Cl.
| | | |
|---|---|---|
| *A61K 31/57* | (2006.01) | |
| *C07J 7/00* | (2006.01) | |
| *C07J 41/00* | (2006.01) | |
| *C30B 7/08* | (2006.01) | |
| *C30B 29/54* | (2006.01) | |

(52) U.S. Cl.
CPC ............. *C07J 41/0083* (2013.01); *C30B 7/08* (2013.01); *C30B 29/54* (2013.01); *C07B 2200/13* (2013.01)

(58) Field of Classification Search
CPC .......................... C07B 2200/13; C07J 41/0083
USPC ............................................ 514/179; 552/598
See application file for complete search history.

(56) References Cited

FOREIGN PATENT DOCUMENTS

| | | |
|---|---|---|
| CN | 102675395 A | 9/2012 |
| CN | 102887931 A | 1/2013 |
| CN | 103193850 A | 7/2013 |
| EP | 1602662 A1 | 12/2005 |
| WO | 89/12448 A1 | 12/1989 |
| WO | 96/30390 A2 | 10/1996 |
| WO | 2004/065405 | 8/2004 |
| WO | 2004/078709 A2 | 9/2004 |
| WO | 2007/144674 A1 | 12/2007 |
| WO | 2010/119029 A1 | 10/2010 |

OTHER PUBLICATIONS

"International Search Report and Written Opinion of the International Searching Authority", Patent Coorperation Treaty International Searching Authority (Feb. 5, 2014), PCT/JP2013/005709, 16 pgs.
"International Search Report and Written Opinion of the International Searching Authority", Patent Coorperation Treaty International Searching Authority (Jan. 28, 2014), PCT/JP2013/005710, 17 pgs.
Rao; et al., "A practical large-scale synthesis of 17alpha-acetoxy-11beta-(4-N,N-dimethylaminophenyl)-19-norpregna-4,9-diene-3,20-dione (CDB-2914)", Steroids (Jul. 2000), 65(7):395-400.

*Primary Examiner* — Barbara P Badio
(74) *Attorney, Agent, or Firm* — Leason Ellis LLP

(57) ABSTRACT

A novel crystalline polymorphic form of ulipristal acetate useful as an agent for preventing and/or treating uterine leiomyoma and as a contraceptive, and a process for producing the crystalline polymorphic form are provided. The novel crystalline polymorphic form of ulipristal acetate is obtained by dissolving an isopropanol-solvated crystal of ulipristal acetate in a mixed solvent containing ethanol and water, and crystallizing an ulipristal acetate from the solution without addition of a seed crystal to the solution.

10 Claims, 3 Drawing Sheets

CRYSTALLINE POLYMORPHIC FORM OF ULIPRISTAL ACETATE

TECHNICAL FIELD

The present invention relates to a novel crystalline polymorphic form of ulipristal acetate, which is useful as a contraception or as an agent for preventing and/or treating uterine leiomyoma or other agents, and relates to a process for producing the crystalline polymorphic form.

BACKGROUND ART

Ulipristal acetate [17alpha-acetoxy-11beta-(4-N,N-dimethylaminophenyl)-19-norpregna-4,9-diene-3,20-dione; hereinafter, may be referred to as UPA], which is a steroid compound possessing antiprogestational activity and antiglucocorticoidal activity, is on the market as an emergency contraceptive drug in the United States and Europe.

As a crystalline ulipristal acetate, for example, Japan Patent No. 2953725 publication (JP-2953725B, PTL 1) discloses a crystalline UPA having a melting point at a temperature of 118 to 121° C. obtained by recrystallization from a mixed solvent of methanol and water. WO96/30390 publication (PTL 2) discloses a crystalline UPA having a melting point at a temperature of 183 to 185° C. obtained by crystallization from diethyl ether. Japanese Patent Application Laid-Open Publication No. 2006-519255 (JP-2006-519255A, PTL 3) discloses a crystalline UPA having a melting point at a temperature of 183 to 185° C. obtained by recrystallization from an ethanol aqueous solution (90%). Japanese Patent Application Laid-Open Publication No. 2006-515869 (JP-2006-515869A, PTL 4) discloses a crystalline UPA having a melting point of 189° C. obtained by recrystallization from an ethanol/water (80/20) mixed solvent. Japanese Patent Application Laid-Open Publication No. 2009-539964 (JP-2009-539964A, PTL 5) discloses a crystalline UPA having a melting point at a temperature of 184 to 186° C. obtained by recrystallization from a mixed solvent of ethanol (230 mL) and water (260 mL).

There is still a need for new crystalline forms of ulipristal acetate having improved solubility and/or improved bioavailability.

CITATION LIST

Patent Literature

PTL 1: JP-2953725B (Claims, Examples)
PTL 2: WO96/30390 publication (Claims, Examples)
PTL 3: JP-2006-519255A (Claims, Examples)
PTL 4: JP-2006-515869A (Claims, Examples)
PTL 5: JP-2009-539964A (Claims, Examples)

SUMMARY OF INVENTION

Technical Problem

It is therefore an object of the present invention to provide a novel crystalline polymorphic form of ulipristal acetate, which is useful as an agent for preventing and/or treating uterine leiomyoma or other agents, and to provide a process for producing the crystalline polymorphic form. The novel crystalline form of ulipristal acetate may be useful as a contraceptive, e.g., an emergency contraceptive. The novel crystalline form of the invention may be also useful as a drug, for instance for treating and/or preventing a gynecological disorder such as uterine fibroids or leiomyoma, endometriosis, uterine bleedings, pain associated with dislocation of endometrium and the like.

It is another object of the present invention to provide a novel crystalline polymorphic form of ulipristal acetate having excellent characteristics (such as solubility, stability, absorption, improved bioavailability), and to provide a process for producing the crystalline polymorphic form.

Solution to Problem

The inventors of the present invention made extensive studies to achieve the above objects and finally found that a wide variety of crystals can be produced by adjusting crystallization conditions of an ulipristal acetate (for example, a crystallization solvent, a method for generating supersaturation, and a drying method); that among these crystals there is a novel crystalline form different in structure from a conventional crystalline form; that the novel crystalline form can be obtained as a single crystalline form without substantial coexistence with other crystalline forms by crystallization under a specific crystallization condition; that an ulipristal acetate substance containing the novel crystalline form has excellent characteristics (e.g., solubility, stability, and absorption) and can improve bioavailability. A crystalline polymorphic form C of ulipristal acetate of the invention may enable to decrease the dosage of ulipristal acetate to administer to the patient so as to obtain the requested or required therapeutic or contraceptive effect. The present invention was accomplished based on the above findings.

A first aspect of the invention is a crystalline form C (crystal C) of ulipristal acetate having an X-ray powder diffraction pattern comprising diffraction peaks at the following diffraction 2theta angles: 9.0±0.2°, 9.3±0.2°, 10.8±0.2°, 11.5±0.2°, 12.2±0.2°, 13.1±0.2°, 14.3±0.2°, 15.6±0.2°, 15.7±0.2°, 15.9±0.2°, 16.6±0.2°, 17.6±0.2°, 17.9±0.2°, 18.9±0.2°, 19.3±0.2°, and 23.8±0.2°.

In some embodiments, said crystalline form C has an X-ray powder diffraction pattern as depicted in FIG. 1 or as described in Table 1. Preferably, the X-ray powder diffraction pattern is obtained with a diffractometer equipped with a Cu K alpha-1 radiation source.

In some additional or other embodiments, the crystalline form C of the invention has a differential scanning calorimetry spectrum, which exhibits an endothermic peak of about 135 to 145° C. The crystalline form C of the invention may further have a differential scanning calorimetry spectrum as depicted in FIG. 2.

Another aspect of the invention is an ulipristal acetate substance comprising the crystalline form C.

It is sufficient that the ulipristal acetate substance (also called herein 'ulipristal acetate mixture') contains the crystalline polymorphic form C. The ulipristal acetate substance may further contain a different crystalline polymorphic form (a crystalline polymorphic form different from the crystalline polymorphic form C) of ulipristal acetate [for example, a crystalline polymorphic form A (crystal A), a crystalline polymorphic form B (crystal B)]. The crystalline polymorphic form A (or the ulipristal acetate substance containing the crystalline polymorphic form A) has an X-ray powder diffraction pattern comprising diffraction peaks at the following diffraction 2theta angles:

9.2±0.2°, 11.4±0.2°, 11.7±0.2°, 12.0±0.2°, 15.2±0.2°, 17.0±0.2°, 17.2±0.2°, and 24.4±0.2°.

The crystalline polymorphic form B (or the ulipristal acetate substance containing the crystalline polymorphic form B) has an X-ray powder diffraction pattern comprising diffraction peaks at the following diffraction 2theta angles:
6.4±0.2°, 8.4±0.2°, 9.4±0.2°, 9.6±0.2°, 11.8±0.2°, 12.8±0.2°, 15.3±0.2°, 16.7±0.2°, 17.5±0.2°, 18.6±0.2°, 19.3±0.2°, 21.0±0.2°, and 25.5±0.2°.

The ratio of the crystalline polymorphic form C relative to the different crystalline polymorphic form (for example, the crystalline polymorphic form A, or the crystalline polymorphic form B) may be about 0.5/99.5 to 99.5/0.5 in a weight ratio of the former/the latter. The above-mentioned weight ratio can be determined based on the relationship between weight ratio and diffraction peak intensities (the height from the baseline of diffraction peak) by measuring the diffraction peak intensities of a reference ulipristal acetate substance containing the crystalline polymorphic form C and other form in a predetermined weight ratio.

The instant invention further relates to a pharmaceutical composition comprising the polymorphic form C or an ulipristal acetate substance according to the invention, and a pharmaceutically acceptable excipient. The pharmaceutical composition may be used as a contraceptive, e.g., as an emergency contraceptive. Alternatively, the pharmaceutical composition of the invention may be used for treating and/or preventing a gynecological disorder such as uterine fibroids, endometriosis, uterine bleedings, pain associated with dislocation of endometrium and the like.

An additional aspect of the invention is a method for producing a crystalline polymorphic form C or an ulipristal acetate substance of the invention.

The process for producing the crystalline polymorphic form C or the ulipristal acetate substance of the present invention comprises dissolving an isopropanol-solvated crystal of ulipristal acetate in a mixed solvent containing ethanol and water, and crystallizing an ulipristal acetate from the solution. In this step, it is preferable that the crystallization of the ulipristal acetate be carried out without addition of a seed crystal to the solution.

Throughout this description, the diffraction angle having a peak (or the peak angle) includes a variable range of ±0.2°.

In the same crystalline form, even if a plurality of peak angles (including a variable range) formally overlaps with each other, each of the peak angles is independent in measurement. For example, the crystalline polymorphic form C has diffraction peaks at
9.0±0.2° and 9.3±0.2°,
and the angle of 9.1 to 9.2° belongs to these two ranges. In this case, it means that there are two different independent peaks at different angles; one peak at 9.0±0.2° and the other at 9.3±0.2°.

Advantageous Effects of Invention

The ulipristal acetate substance and the polymorphic form C of the present invention have a higher solubility and more excellent stability and absorption compared with a conventional crystalline form, and can improve bioavailability. Moreover, the ulipristal acetate substance and the polymorphic form C of the present invention are useful as an agent for preventing and/or treating uterine leiomyoma or other agents and also have an excellent safety as medicine (or pharmaceutical preparation). The ulipristal acetate substance and the polymorphic form C of the invention are useful as contraceptive.

DESCRIPTION OF EMBODIMENTS

[Ulipristal acetate substance] As used herein, an ulipristal acetate substance refers to ulipristal acetate in the form of a mixture or composition of polymorphic forms. An ulipristal acetate substance according to the invention comprises at least polymorphic form C. In some embodiments, the ulipristal acetate substance according to the invention comprises at least 5% by weight of the polymorphic form C, the weight percentage referring to the total weight of the ulipristal acetate substance.

As used herein, at least 5% by weight of the polymorphic form C encompasses at least 10%, at least 20%, at least 30%, at least 40%, at least 50%, at least 60%, at least 70% at least 80% at least 90% by weight of the polymorphic form C. In a preferred embodiment, the polymorphic form C is the main polymorphic form of ulipristal acetate present within the ulipristal acetate substance of the invention. This means that the ulipristal acetate substance of the invention comprises no less than 50% by weight of polymorphic form C, preferably at least 90%, more preferably at least 95%, and even more preferably at least 99.5% by weight of polymorphic form C. The remaining polymorphic forms present in the ulipristal acetate substance of the invention may be an amorphous form of ulipristal acetate or any crystalline forms of ulipristal acetate. In some embodiments, the ulipristal acetate substance of the invention essentially consists in polymorphic form C as described herein.

The ulipristal acetate substance is characterized by a diffraction peak in X-ray powder diffraction pattern. Specifically, the ulipristal acetate substance contains at least a crystalline polymorphic form C of ulipristal acetate (crystal C) and has at least a diffraction pattern derived from the crystalline polymorphic form C in an X-ray powder diffraction spectrum.

The crystalline polymorphic form C has diffraction peaks at a diffraction angle 2theta of at least
9.0±0.2°, 9.3±0.2°, and 15.7±0.2°
in an X-ray powder diffraction spectrum. These diffraction peaks are usually ranked in the top three intensities in many cases. The diffraction peak at
9.3±0.2°
may show the largest intensity. The preferred crystalline polymorphic form C has diffraction peaks at the following diffraction angle 2theta in an X-ray powder diffraction spectrum:
9.0±0.2°, 9.3±0.2°, 10.8±0.2°, 11.5±0.2°, 12.2±0.2°, 13.1±0.2°, 14.3±0.2°, 15.6±0.2°, 15.7±0.2°, 15.9±0.2°, 16.6±0.2°, 17.6±0.2°, 17.9±0.2°, 18.9±0.2°, 19.3±0.2°, and 23.8±0.2°.

Figure 1:
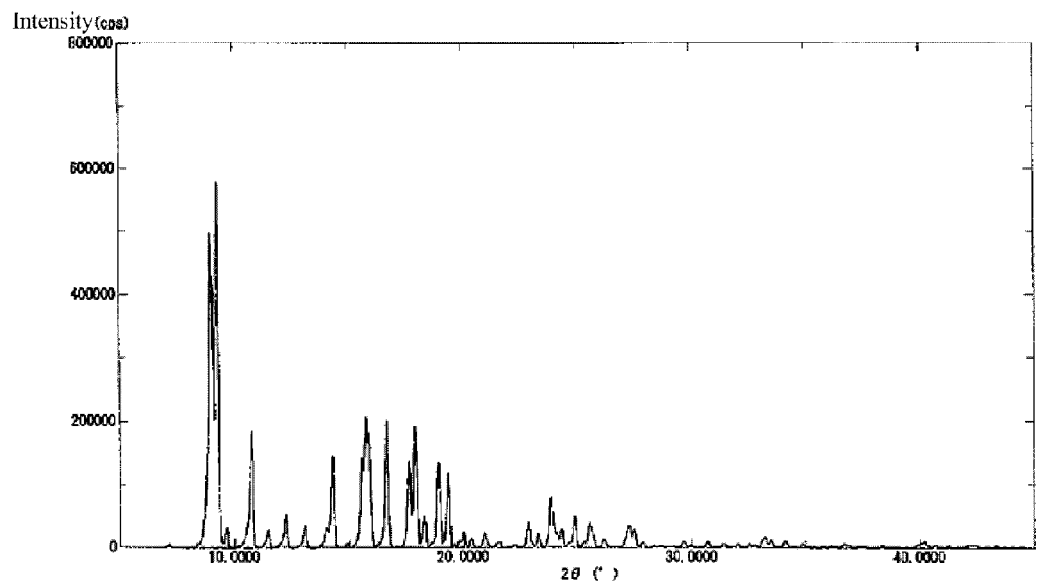
FIG. 1 is a graph showing an X-ray powder diffraction spectrum of a crystalline polymorphic form C of Example 1.

In some embodiments, the crystalline form C of the invention has a X-ray diffraction pattern as depicted in FIG. 1 or as described in Table 1.

The X-ray powder diffraction spectrum can be measured according to a common method, preferably using a diffractometer with Cu K alpha-1 radiation source, for example, the condition of Examples mentioned below. The diffraction angle 2theta of the diffraction peak sometimes varies within a range of about ±0.2° (e.g., about)±0.1° depending on the measurement conditions and the state of samples. However, the same crystal structure has almost the same X-ray powder diffraction pattern without significant change in the number of characteristic diffraction peaks.

The ulipristal acetate substance is characterized by peak(s) in a differential scanning calorimetry spectrum. Specifically, the ulipristal acetate substance has peak(s) derived from at least the crystalline polymorphic form C in a differential scanning calorimetry spectrum.

The crystalline polymorphic form C may have an endothermic peak (or melting point) at about 135 to 145° C. (e.g., about 137 to 143° C., preferably about 139 to 141° C.) in the differential scanning calorimetry spectrum. Moreover, the crystalline polymorphic form C may have an exothermic peak at about 145 to 170° C. (e.g., about 160 to 167° C., preferably about 163 to 165° C.). It is presumed that the exothermic peak is a peak due to transition to the crystalline polymorphic form A from the crystalline polymorphic form C. Further, the crystalline polymorphic form C may have an endothermic peak at about 180 to 192° C. and preferably about 183 to 190° C. It is presumed that the endothermic peak is a peak due to melting of the transited crystalline polymorphic form A.

Figure 2:
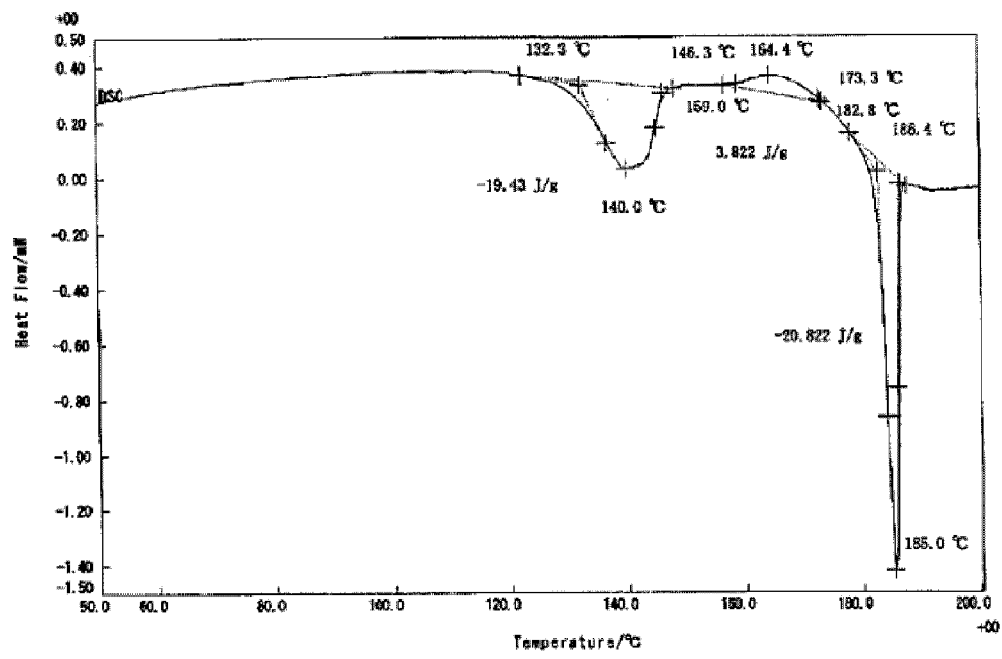
FIG. 2 is a graph showing a differential scanning calorimetry spectrum of the crystalline polymorphic form C of Example 1.

In some embodiments, the polymorphic form C of the invention has differential scanning calorimetry spectrum as depicted in FIG. 2.

It is sufficient that the ulipristal acetate substance of the invention contains the crystalline polymorphic form C. The ulipristal acetate substance of the invention may further contain a different crystalline ulipristal acetate (polymorphic crystal of ulipristal acetate). The ulipristal acetate substance of the invention may further contain amorphous ulipristal acetate and/or a crystalline ulipristal acetate distinct from form C. Examples of the different crystalline polymorphic form may include a crystalline polymorphic form having a diffraction peak in diffraction angle range different from that in the crystalline polymorphic form C in an X-ray powder diffraction spectrum, for example, (1) a crystalline polymorphic form A (crystal A) of an ulipristal acetate having an X-ray powder diffraction spectrum comprising diffraction peaks at the following diffraction angle 2theta:

9.2±0.2°, 11.4±0.2°, 11.7±0.2°, 12.0±0.2°, 15.2±0.2°, 17.0±0.2°, 17.2±0.2°, and 24.4±0.2°;
and (2) a crystalline polymorphic form B (crystal B) of an ulipristal acetate having an X-ray powder diffraction spectrum comprising diffraction peaks at the following diffraction angle 2theta:

6.4±0.2°, 8.4±0.2°, 9.4±0.2°, 9.6±0.2°, 11.8±0.2°, 12.8±0.2°, 15.3±0.2°, 16.7±0.2°, 17.5±0.2°, 18.6±0.2°, 19.3±0.2°, 21.0±0.2°, and 25.5±0.2°.

As the different crystalline polymorphic form, there may be mentioned a crystalline polymorphic form having an endothermic peak (or melting point) in a temperature range different from that in the crystalline polymorphic form C in a differential scanning calorimetry spectrum, for example, a crystalline polymorphic form A having an endothermic peak (or melting point) at about 180 to 192° C. (preferably about 183 to 190° C.), a crystalline polymorphic form B having an endothermic peak (or melting point) at about 160 to 170° C. (e.g., about 165 to 169° C., preferably about 166 to 168° C.).

Figure 3:
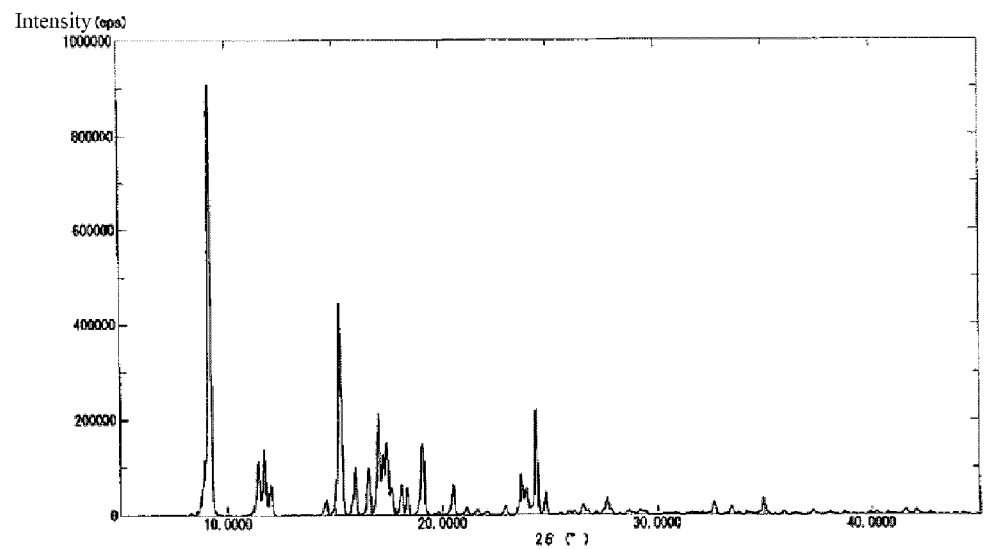
FIG. 3 is a graph showing an X-ray powder diffraction spectrum of a crystalline polymorphic form A of Example 2.
Figure 4:
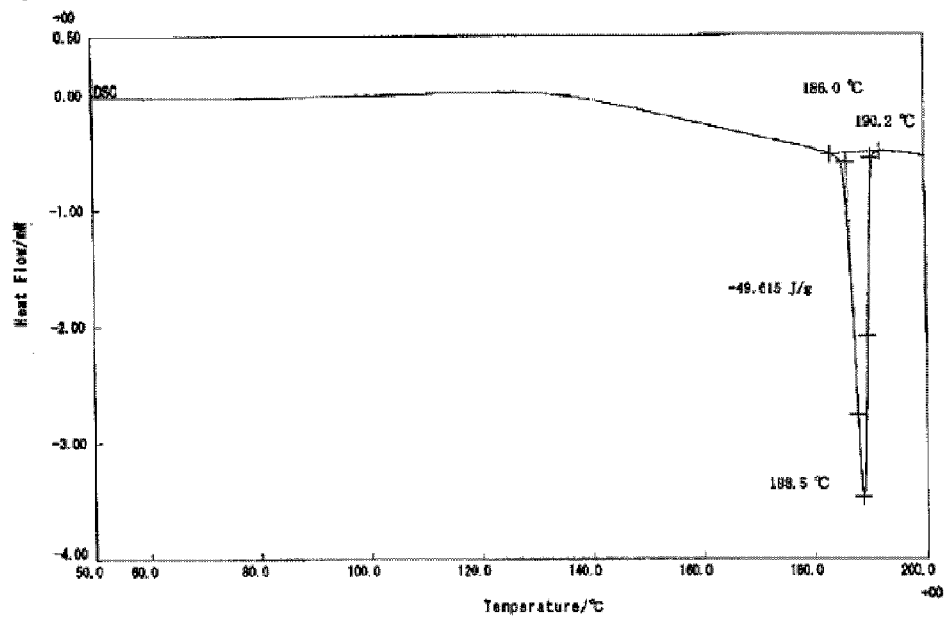
FIG. 4 is a graph showing a differential scanning calorimetry spectrum of the crystalline polymorphic form A of Example 2.
Figure 5:
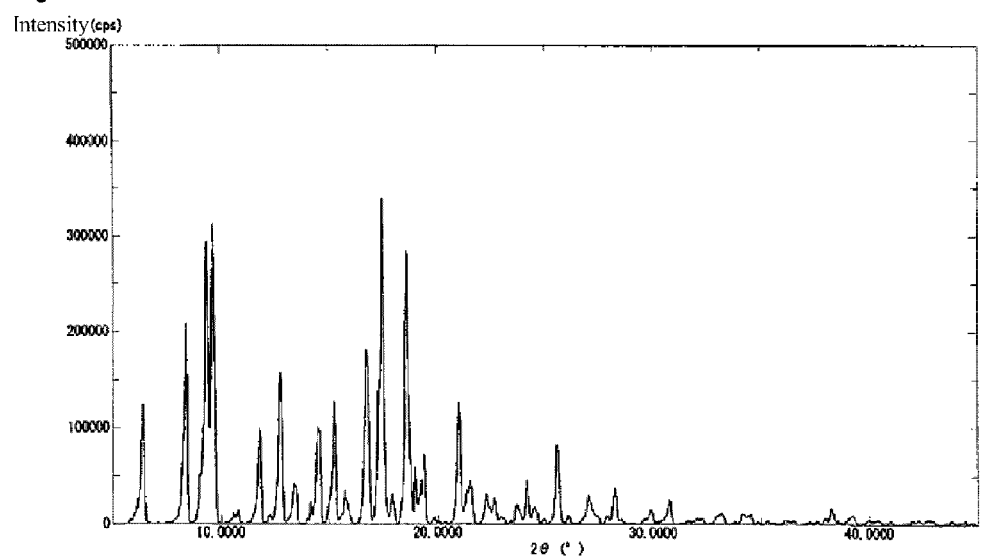
FIG. 5 is a graph showing an X-ray powder diffraction spectrum of a crystalline polymorphic form B of Example 3.
Figure 6:
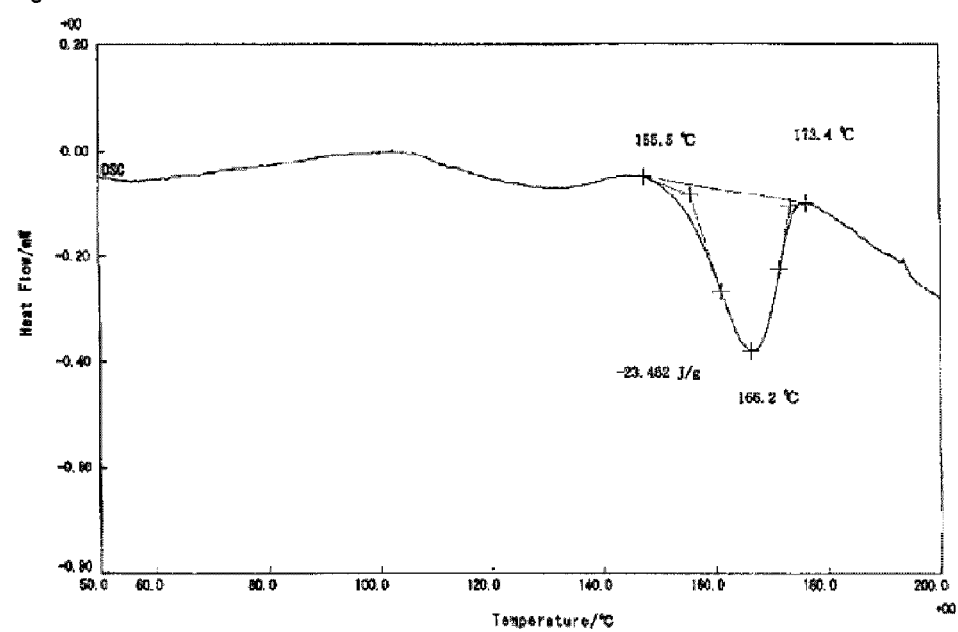
FIG. 6 is a graph showing a differential scanning calorimetry spectrum of the crystalline polymorphic form B of Example 3.

For instance, the crystalline form A may have the X-ray powder diffraction pattern as depicted in FIG. 3 or described in Table 2 and/or the differential scanning calorimetry spectrum as shown in FIG. 4. The crystalline form B may have the X-ray powder diffraction pattern as shown in FIG. 5 or described in Table 3 and/or the differential scanning calorimetry spectrum as shown in FIG. 6.

The different crystalline polymorphic forms may be used alone or in combination. Among the different crystalline polymorphic forms, the crystalline polymorphic form B is preferred in terms of solubility.

The ratio (weight ratio) of the crystalline polymorphic form C relative to the different crystalline polymorphic form (such as the crystalline polymorphic form A or the crystalline polymorphic form B) is not particularly limited to a specific one, and can be selected from the range of about 0.5/99.5 to 99.5/0.5 (e.g., about 1/99 to 99/1) in a ratio of the former/the latter. For example, the ratio may be about 10/90 to 99.5/0.5 (e.g., about 20/80 to 99.5/0.5), preferably about 30/70 to 99/1 (e.g., about 40/60 to 99/1), and more preferably about 50/50 to 99/1 (e.g., about 60/40 to 95/5, preferably about 70/30 to 90/10).

The ulipristal acetate substance (ulipristal acetate mixture or mixed crystal) containing the crystalline polymorphic form C and the different crystalline polymorphic form has structural characteristics derived from these respective crystalline forms (e.g., a diffraction peak in an X-ray powder diffraction spectrum, an endothermic peak in a differential scanning calorimetry spectrum). Incidentally, the intensity ratio of the diffraction peaks (or the endothermic peaks) of these respective crystalline forms often corresponds to the mixing ratio of these respective crystalline forms.

The ulipristal acetate substance (or each crystalline polymorphic form) may contain a low molecular weight compound (or a solvent) [or a low molecular weight compound (or a solvent) may adhere to the ulipristal acetate]. The low molecular weight compound (or the solvent) is not particularly limited to a specific one as far as the low molecular weight compound (or the solvent) is pharmaceutically acceptable. For example, the low molecular weight compound (or the solvent) may include water and an organic solvent [for example, an aliphatic hydrocarbon (e.g., hexane), an aromatic hydrocarbon (e.g., toluene), an alcohol (e.g., a $C_{1-4}$alkanol such as ethanol, 1-propanol, or isopropanol), an ether (e.g., an acyclic ether such as diethyl ether; a cyclic ether such as dioxane or tetrahydrofuran), a ketone (e.g., acetone and methyl ethyl ketone), an ester (e.g., a formate and an acetate), an amide (e.g., dimethylformamide and dimethylacetamide), a sulfoxide (e.g., dimethylsulfoxide), and a cyclic amine (e.g., pyridine)]. These low molecular weight compounds (or solvents) may be used alone or in combination. The amount of the low molecular weight compound (or the adhering amount thereof) relative to 100 parts by weight of the ulipristal acetate (or each crystalline polymorphic form) may for example be about not more than 30 parts by weight, preferably about not more than 20 parts by weight, and more preferably about not more than 10 parts by weight (e.g., about 0.001 to 1 parts by weight).

The ulipristal acetate substance (or each crystalline polymorphic form) may be a single crystal or may be a twin crystal or a polycrystal. The form (external form) of the ulipristal acetate substance (or each crystalline polymorphic form) is not particularly limited to a specific one. For example, the form of the crystalline ulipristal acetate may be triclinic, monoclinic, rhombic (orthorhombic), tetragonal, cubic, trigonal (rhombohedral), hexagonal, or other forms. The crystalline ulipristal acetate may be a spherulite, a skeleton crystal, a dendrite, a needle crystal (for example, a crystal whisker), or others.

The particle size of the ulipristal acetate substance or the polymorphic form C is not particularly limited to a specific one. For example, the average particle size (average particle diameter) of the ulipristal acetate substance or the polymorphic form C based on a laser diffraction may be about 0.5 micrometers to 1 millimeter and preferably about 1 to 500 micrometers (e.g., about 2 to 100 micrometers) or is usually about 5 to 50 micrometers (e.g., about 5 to 30 micrometers). The ulipristal acetate substance or the polymorphic form C of the invention may be micronized.

The ulipristal acetate substance or the polymorphic form C of the invention is highly soluble in a solvent and has an excellent bioavailability. For example, the solubility of the ulipristal acetate substance or the polymorphic form C in a mixed solvent of ethanol and water [ethanol/water (volume ratio)=10/90] may be about 7 to 30 micrograms/mL, preferably about 8 to 27 micrograms/mL, and more preferably about 9 to 25 micrograms/mL (e.g., about 10 to 25 micrograms/mL) at 37° C.

[Process for producing ulipristal acetate substance or polymorphic form C] The process for producing the ulipristal acetate substance or the polymorphic form C of the invention is not particularly limited to a specific one as far as a crystal characterized by the above-mentioned X-ray powder diffraction spectrum or differential scanning calorimetry spectrum can be obtained. The process for producing the ulipristal acetate substance or the polymorphic form C of the invention comprises, for example, a step for dissolving an isopropanol-solvated crystal of ulipristal acetate in a mixed solvent containing ethanol and water and crystallizing (precipitating or depositing) an ulipristal acetate from the solution (or crystallization system).

The isopropanol content (the degree of isopropanol solvation) of the isopropanol-solvated crystal of ulipristal acetate may for example be about 0.5 to 5 mol, preferably about 0.5 to 2.5 mol, and more preferably about 0.5 to 1 mol (e.g., about 0.5 mol) relative to 1 mol of the ulipristal acetate.

The isopropanol-solvated crystal of ulipristal acetate can be produced by a common method, for example, by allowing 3,3-(1,2-ethanedioxy)-5alpha-hydroxy-11beta-(4-N,N-dimethylaminophenyl)-17alpha-acetoxy-19-norpregna-9-ene-20-one to react with an acid (for example, an organic acid such as acetic acid or trifluoroacetic acid; and an inorganic acid such as hydrochloric acid, sulfuric acid, monopotassium sulfate, or phosphoric acid), dissolving the reaction mixture [or a crude purified product obtained by purifying the reaction mixture with a common purification means (such as filtration, centrifugation, chromatography, or recrystallization)] in isopropanol, and crystallizing an ulipristal acetate from the solution. In order to obtain the isopropanol-solvated crystal certainly, it is preferable that the crystallization step be repeated a plurality of times (for example, twice to four times). The details of the production process of the isopropanol-solvated crystal may for example be referred to Japanese Patent Application Laid-Open Publication No. 2006-515869, or others.

In the mixed solvent, the ratio (volume ratio) of ethanol relative to water may for example be about 70/30 to 90/10, preferably about 72/28 to 88/12, and more preferably about 75/25 to 85/15 in a ratio of the former/the latter. The ratio of the mixed solvent relative to 1 g of the isopropanol-solvated crystal of ulipristal acetate may for example be about 0.5 to 50 mL, preferably about 1 to 20 mL, and more preferably about 5 to 15 mL.

The method for crystallizing (recrystallizing or separating) an ulipristal acetate from the solution (or crystallization system) may include a cooling method (a method which comprises cooling a crystallization system), a poor-solvent addition method (a method which comprises adding a poor solvent for an ulipristal acetate to a crystallization system), and others. The preferred method includes the cooling method. For the cooling method, the cooling rate is not particularly limited to a specific one. The cooling may be slow cooling or rapid cooling. The preferred cooling is slow cooling. For example, the cooling rate may for example be about 0.01 to 5° C./minute, preferably about 0.05 to 3° C./minute, and more preferably about 0.1 to 1° C./minute.

In order to obtain the crystalline polymorphic form C without substantial coexistence with other crystalline forms in crystallization, it is preferable that a seed crystal be not added to the solution of the isopropanol-solvated crystal of ulipristal acetate (or the crystallization system).

The step of dissolving the ulipristal acetate crystal in the mixed solvent and crystallizing (or recrystallizing) the ulipristal acetate from the solution may be conducted repeatedly a plurality of times (for example, twice to four times). Moreover, after crystallization (or recrystallization), the resulting product may be dried (such as by air drying, through circulation drying, or drying under a reduced pressure). The resulting product is usually dried under a reduced pressure [for example, dried under not more than 50 hPa, preferably not more than 20 hPa (e.g., about 1 to 15 hPa)]. The drying temperature may be a room temperature to a heated temperature, preferably about 25 to 120° C. (e.g., about 50 to 120° C.), and more preferably about 30 to 110° C. (e.g., about 80 to 110° C.). The drying time may for example be about 1 to 24 hours (e.g., about 5 to 24 hours) and preferably about 1 to 20 hours (e.g., about 10 to 20 hours).

According to the above-mentioned step, the crystalline polymorphic form C may be prepared as a single form.

A method for preparing an ulipristal acetate substance may comprise the steps of:
  a) providing the crystalline form C of the invention,
  b) providing one or several polymorphic form(s) of ulipristal acetate, and
  c) mixing the crystalline form C with polymorphic form(s) provided in step b.

In some embodiment, the method for preparing an ulipristal acetate substance may comprise the steps of forming the different crystalline polymorphic form by crystallization or transition (transformation) in association with the solvent (precipitation from the solution, condensation of the solution, transition in the solution or dispersion medium) and mixing the crystalline polymorphic form C and the different crystalline polymorphic form.

The raw ulipristal acetate to be subjected to the step for forming the different crystalline polymorphic form may include the reaction mixture (or the crude purified product obtained by purifying the reaction mixture with a common purification means) as described in the production process of the isopropanol-solvated crystal of ulipristal acetate, and others.

The solvent (or crystallization solvent) may include water, an organic solvent [for example, an aliphatic hydrocarbon (e.g., an acyclic aliphatic hydrocarbon such as hexane; and an alicyclic hydrocarbon such as cyclohexane), an aromatic hydrocarbon (e.g., toluene), an alcohol (e.g., an $C_{1-4}$alkanol such as ethanol, 1-propanol, 2-propanol, or 1-butanol), an ester (e.g., ethyl formate, ethyl acetate, isopropyl acetate, and isobutyl acetate), a ketone (e.g., acetone and methyl ethyl ketone), an ether (e.g., an acyclic ether such as diethyl ether; and a cyclic ether such as dioxane or tetrahydrofuran), a sulfoxide (e.g., dimethylsulfoxide), an amide (e.g., an N-alkylacylamide such as N,N-dimethylformamide or N,N-dimethylacetamide), a nitrile (e.g., an alkanenitrile such as acetonitrile), a cyclic amine (e.g., pyridine)], and others. These solvents may be used alone or in combination.

The ratio of the solvent relative to 1 g of the raw ulipristal acetate may for example be about 0.1 to 500 mL, preferably about 0.5 to 400 mL, and more preferably about 1 to 300 mL (e.g., about 2 to 200 mL).

Examples of the method for forming the different crystalline polymorphic form may include a cooling method, a poor-solvent addition method, a seed crystal addition method (a method which comprises dissolving a raw ulipristal acetate in a solvent and adding a seed crystal of ulipristal acetate to the solution), an evaporation method (a method which comprises dissolving a raw ulipristal acetate in a solvent and condensing the solution), and a stir-suspension method (a method which comprises changing a crystalline form of an ulipristal acetate in a state that the ulipristal acetate is dispersed in a solvent).

Among the different crystalline polymorphic forms, the crystalline polymorphic form A may for example be prepared by dissolving an isopropanol-solvated crystal of ulipristal acetate in a mixed solvent containing ethanol and water and adding a seed crystal (crystalline polymorphic form A or B) to the solution for crystallization. Moreover, the crystalline polymorphic form B may for example be prepared by dissolving the raw ulipristal acetate in ethanol and cooling (rapidly cooling) the solution, or may be prepared by dissolving the raw ulipristal acetate in at least one solvent selected from the group consisting of ethanol, 1-propanol, and ethyl acetate and condensing the solution.

Incidentally, in the mixed solvent containing ethanol and water used for the production of the crystal A, the ratio (volume ratio) of ethanol relative to water may for example be about 75/25 to 85/15 in a ratio of the former/the latter.

[Use and pharmaceutical composition] Since the crystalline form C or the ulipristal acetate substance of the present invention has not only an antiprogestational activity but also an antiglucocorticoidal activity, the crystalline form C or the ulipristal acetate substance is preferably used as a selective progesterone receptor modulator. Specifically, the crystalline form C or the ulipristal acetate substance of the present invention is useful for preventing and/or treating of a gynecological disease [for example, uterine leiomyoma or a disease attributable to uterine leiomyoma (e.g., metastatic leiomyoma, dysmenorrhea, menorrhagia, anemia, infertility, constipation, pollakiuria, and lumbago)]. Moreover, the crystalline form C or the ulipristal acetate substance of the present invention is also useful as a contraceptive agent, for example an emergency contraceptive agent.

The crystalline form C or the ulipristal acetate substance of the invention may be also useful as a drug, for instance for treating and/or preventing a gynecological disorder. As used herein, gynecological disorders encompass, without being limited to, uterine fibroids or leiomyoma, endometriosis, uterine bleedings, pain associated with dislocation of endometrium and the like.

The invention also relates to a method for treating a female patient preferably suffering from a gynecological disorder comprising administering a therapeutic effective amount of the crystalline form C or that of the ulipristal acetate substance of the invention to said patient.

A further aspect of the invention is a method for providing contraception to a woman in need thereof, comprising administering said woman with a contraceptive amount of the polymorphic form C or the ulipristal acetate substance of the invention.

The contraceptive method of the invention may be an emergency contraceptive method wherein the administration of the polymorphic form C or that of the ulipristal acetate substance of the invention occurs within 120 hours after an unprotected intercourse. Alternatively, the contraceptive method may be a regular contraceptive method wherein the administration of ulipristal acetate is repeated several days in a row within the menstrual cycle. Alternatively, the contraceptive method of the invention may be an on-demand contraception method as described in WO2010/119029, the disclosure of which being incorporated by reference. Preferably, the administration of ulipristal acetate in contraceptive methods of the invention is oral.

The invention also relates to the use of the polymorphic form C or that of the ulipristal acetate substance of the invention in the manufacture of a contraceptive or in the manufacture of a drug for treating a gynecological disorder.

The above-mentioned crystalline form C or the ulipristal acetate substance may be used as a medicine alone, or the above-mentioned crystalline form C or the ulipristal acetate substance may be used in combination with a carrier (e.g., a pharmacologically or physiologically acceptable carrier) to provide a pharmaceutical composition (or a preparation).

In a further aspect, the invention relates to a pharmaceutical composition comprising the polymorphic form C or the ulipristal acetate substance of the invention and a pharmaceutically acceptable excipient. In some embodiments, the pharmaceutical composition of the invention is such that at least 5% by total weight of the ulipristal acetate present in the pharmaceutical composition is polymorphic form C. In some further embodiments, polymorphic form C is the main polymorphic form of ulipristal acetate present within the composition. This means that the pharmaceutical composition of the invention may comprise no less 50% of polymorphic form C with respect to total weight of ulipristal acetate present within the composition. In some embodiments polymorphic form C accounts for at least 60%, preferably at least 80% and even at least 90% by weight with respect to the total weight of ulipristal acetate present within the composition.

The pharmaceutical composition may comprise from 0.01% to 80% by weight of the polymorphic form C or the ulipristal acetate substance of the invention and from 20% to 99.99% by weight of excipient(s).

With respect to the pharmaceutical composition of the present invention, the excipient(s) may be suitably selected depending on the form of the composition or preparation (that is, the dosage form), the route of administration, the application (or use), and others. The dosage form is not particularly limited to a specific one and may be a solid preparation (for example, powdered preparations, powders, granulated preparations (e.g., granules and microfine granules or the like), spherical or spheroidal preparations, pills, tablets, capsules (including soft capsules and hard capsules), dry syrups, and suppositories), a semisolid preparation (for example, creams, ointments, gels, gumdrop-like preparations, and film-like preparations, sheet-like preparations), a liquid preparation (for example, solutions, suspensions, emulsions, syrup, elixir, lotions, injectable solutions (or injections), and drops), and others. Moreover, sprays or aerosols of the powdered preparations and/or the liquid preparation may be also included. Incidentally, the capsules may be a capsule filled with a liquid or a capsule filled with a solid preparation (such as granules). Moreover, the preparation may be a lyophilized preparation. Further, the preparation of the present invention may be a preparation releasing the active ingredient(s) at a controlled rate (a sustained release preparation or a rapid-release preparation). Moreover, the preparation may be an oral dosage form [for example, granules, powders, tablets (e.g., sublingual tablets and orally disintegrating tablets), capsules, syrup, emulsions, suspensions, jellys, gumdrop-like preparations, and film preparations] or a parenteral dosage form (for example, inhalants, preparations for transdermal administration, and preparations for transnasal administration). Furthermore, the preparation may be topical or local administration form [for example, injections (e.g., hypodermic injections, intravenous injections, intramuscular injections, and intraabdominal injections), suspensions, ointments, plasters and pressure sensitive adhesives, cataplasms.

The excipient(s) may suitably be selected, for example, depending on the administration route and the application of preparation, from components (e.g., a diluent, a binder, a disintegrant, a lubricant, and a coating agent) listed in Japanese Pharmacopoeia, (1) Handbook of Pharmaceutical Excipients (Maruzen Company, ltd., (1989)), (2) Japanese Pharmaceutical Excipients Dictionary 2007 (Yakuji Nippo Ltd., issued July, 2007), (3) Pharmaceutics, revised fifth edition (Nankodo, Co., Ltd. (1997)), and (4) Japanese Pharmaceutical Excipients 2003 (Yakuji Nippo Ltd., issued August, 2003). For example, the excipient for a solid preparation is practically at least one member selected from the group consisting of a diluent, a binder, and a disintegrant. Moreover, the pharmaceutical composition may contain a lipid.

The diluent may include a saccharide or a sugar alcohol such as lactose, glucose, sucrose, mannitol, sorbitol, or xylitol; a starch such as a corn starch; a polysaccharide such as a crystalline cellulose (including a microcrystalline cellulose); silicon dioxide or a silicate such as a light silicic anhydride; and others. The binder may include a soluble starch such as a pregelatinized starch or a partially pregelatinized starch; a polysaccharide such as gum acacia (or gum arabic), dextrin, or sodium alginate; a synthetic polymer such as a polyvinylpyrrolidone (PVP), a polyvinyl alcohol (PVA), a carboxyvinyl polymer, a polyacrylic polymer, a polylactic acid, or a polyethylene glycol; a cellulose ether such as a methyl cellulose (MC), an ethyl cellulose (EC), a carboxymethyl cellulose (CMC), a carboxymethyl cellulose sodium, a hydroxyethyl cellulose (HEC), a hydroxypropyl cellulose (HPC), or a hydroxypropylmethyl cellulose (HPMC); and others. The disintegrant may include a sodium carboxymethyl starch, a carmellose, a carmellose sodium, a carmellose calcium, a croscarmellose sodium, a crospovidone, a low-substituted hydroxypropyl cellulose, and others. These excipients may be used alone or in combination.

The pharmaceutical composition may be a coated form. For example, there may be used, as the coating agent, a saccharide or a sugar, a cellulose derivative such as an ethyl cellulose or a hydroxymethyl cellulose, a poly(oxyethylene glycol), a cellulose acetate phthalate, a hydroxypropylmethyl cellulose phthalate, a methyl methacrylate-(meth) acrylic acid copolymer, and eudragit (a copolymer of methacrylic acid and acrylic acid). The coating agent may be an enteric component (e.g., a cellulose phthalate, a hydroxypropylmethyl cellulose phthalate, and a methyl methacrylate-(meth)acrylic acid copolymer) or a gastric soluble component comprising a polymer (e.g., eudragit) containing a basic component such as a dialky-laminoalkyl(meth)acrylate. Moreover, the preparation may be a capsule having such an enteric component or gastric soluble component as a capsule shell. Alternatively, the pharmaceutical composition may be a coated or uncoated tablet.

In the preparation, known additives can be suitably used depending on an administration route, a dosage form, and others. Such an additive may include, for example, a lubricant, a disintegrant aid, an antioxidation agent or an antioxidant, an emulsifier, a dispersing agent, a suspending agent, a dissolving agent, a dissolution aid, a thickener, a pH adjusting agent or a buffer, a stabilizer, an antiseptic agent or a preservative, a fungicide or antibacterial agent, an antistatic agent, a corrigent or a masking agent, a coloring agent, a deodorant or a perfume, an algefacient, an antifoaming agent, an isotonizing agent, and a soothing agent. These additives may be used alone or in combination.

The pharmaceutical composition (or pharmaceutical preparation) of the present invention may contain other physiologically active components or pharmacologically active components (for example, a follicle hormone (or an estrogen preparation)) if necessary.

The pharmaceutical composition of the present invention may be prepared by using an excipient component in addition to an effective ingredient, and if necessary, an additive and the like, with a conventional preparation manner (for example, a production process described in Japanese Pharmacopoeia 16th edition or a process in accordance with the production process).

The pharmaceutical composition may comprise from 1 mg to 50 mg, preferably from 5 mg to 40 mg of ulipristal acetate per dosage unit, for instance 5, 10, 15, 20 or 30 mg per dosage unit.

The crystalline form C or the ulipristal acetate substance of the present invention (also including the agent for preventing and/or treating a gynecological disease, the contraceptive, and the pharmaceutical composition), which has a low toxicity and an excellent safety, is safely administered to female human beings and non-humans, usually mammals (for example, human beings, mice, rats, rabbits, dogs, cats, bovines, horses, pigs, and monkeys). The amount to be administered (or dose) may be selected according to the species, age, body weight, and condition (e.g., a performance status, a condition of a disease, a presence of a complication) of the subject to be administered, the duration (or period or schedule) of administration, the dosage form, the method (or route) of administration, and others. For example, the amount to be administered (or dose) to human beings (daily dose) is about 1 to 50 mg/day and preferably about 5 to 40 mg/day.

The method (or route) of administration may be an oral administration or a local or parenteral administration (for example, hypodermic administration, intravenous administration, intramuscular administration, transrectal administration, and transvaginal administration).

The frequency of administration is not particularly limited to a specific one. For example, the frequency of administration may be once a day or if necessary may be a plurality times a day (e.g., twice to three times a day).

EXAMPLES

The following examples are intended to describe this invention in further detail and should by no means be interpreted as defining the scope of the invention.

[X-ray powder diffraction spectrum] The X-ray powder diffraction spectrum was measured under the following conditions: radiation source: Cu K(alpha1), tube voltage: 40 kV, tube current: 40 mA, sampling interval: 0.1°, scanning speed: 10°/minute. In the X-ray powder diffraction chart, the diffraction peak was searched by second order differential as a peak width threshold of 0.1°.

[Differential scanning calorimetry spectrum] The differential scanning calorimetry spectrum was measured using a differential scanning calorimeter (type: DSC8230L) at a rate of heating of 2° C./minute.

[Solubility] For each of ulipristal acetate samples obtained in Examples and Comparative Example, the solubility was determined as follows. The ulipristal acetate (40 mg) was added to 40 mL of a mixed solvent containing ethanol and water [ethanol/water (volume ratio)=10/90] having a temperature of 37° C. to prepare a test sample. The test sample was stirred by a magnetic stirrer for 5 minutes. Then a portion of the suspension was separated. The solid of the separated portion was filtered out, and the ulipristal acetate content of the residue was quantitatively determined using a high-performance liquid chromatography (column: ODS, column temperature: 40° C., eluate: 0.1% trifluoroacetic acid aqueous solution/acetonitrile mixture (volume ratio 3:2), rate of flow: 1.0 mL/minute, detection: UV 302 nm), and the solubility was calculated.

[Absorption test in dog] For each of ulipristal acetate samples obtained in Examples and Comparative Example, the absorption test was performed as follows. The ulipristal acetate was filled into a gelatin capsule shell (manufacturer: Qualicaps Co., Ltd., size: No. 00, lot: C0079A) to produce a capsule. The capsule was orally administered to 6 female dogs at a dose of 25 mg/kg (in terms of ulipristal acetate). The blood was collected 0.5, 1, 2, 4, 6, 24, and 48 hours after the oral administration. Then the sample was centrifuged to give a plasma. The concentration of the ulipristal acetate in the plasma was measured by a LC-MS/MS (liquid chromatography-tandem mass spectrometry) method, and the elimination half-life ($T_{1/2}$), the time to the maximum plasma concentration ($T_{max}$), the maximum plasma concentration ($C_{max}$), the area under the plasma concentration-time curve (AUC), and the mean residence time (MRT) were calculated. The capsule was administered to each female dog twice at dosing intervals (washout period) of one week by crossover method.

COMPARATIVE EXAMPLE 38.5 g of 3,3-(1,2-ethanedioxy)-5alpha-hydroxy-11beta-(4-N,N-dimethylaminophenyl)-17alpha-acetoxy-19-nor-pregna-9-ene-20-one [carbinol acetate] was loaded into a flask under nitrogen atmosphere at a temperature of 20 to 22° C., and 385 mL of deionized water and 17.91 g of potassium bisulfate were added. The obtained suspension was stirred until complete dissolution, for about 4 hours. The end of the reaction was determined by means of thin layer chromatography (TLC).

To the reaction solution was added 3.85 g of neutral $Al_2O_3$, the mixture was stirred for 30 minutes, the suspension was filtered and the insoluble particles were washed with 38.5 mL of deionized water. To the filtrate was added 325 mL of ethyl acetate, and the pH was adjusted to a value between 7.0 to 7.2 with a 7% (w/v) sodium bi-carbonate solution. The mixture was allowed to stand for 15 minutes, the phases were separated, discharging the aqueous phase. To the resulting organic phase was added 192.5 mL of deionized water, the mixture was stirred for 10 minutes and then allowed to stand for 15 minutes. The phases were separated, discharging the aqueous phase.

The resulting organic phase was vacuum-concentrated to give a raw ulipristal acetate residue. To the residue was added 38.5 mL of isopropanol, and the mixture was vacuum-concentrated. To the resulting residue was added the same amount (38.5 mL) of isopropanol, the mixture was vacuum-concentrated again. To the resulting solid product was added 77 mL of isopropanol, and the mixture was heated for dissolution. The solution was allowed to cool to 0 to 5° C., and the temperature was maintained for one hour. The obtained suspension was filtered and the cake was washed with cold isopropanol to give an isopropanol hemisolvate crystal at a yield of 96% by mol.

By using the isopropanol hemisolvate crystal (10 g), an ulipristal acetate was crys-tallized in accordance with Japanese Patent Application Laid-Open Publication No. 2006-515869 (JP-2006-515869A) to give 7.5 g of a crystalline polymorphic form A of ulipristal acetate (crystal A), which had a melting point of 189° C.

Example 1

The ulipristal acetate crystal (1.761 g) obtained in Comparative Example was dissolved in 10 mL of isopropanol by heating, and the solvent was distilled off under a reduced pressure. The resulting residue was dissolved in 9 mL of isopropanol by heating, and the solvent was distilled off under a reduced pressure. The resulting residue was dissolved in 9 mL of isopropanol by heating, and the solution was allowed to stand in ice-water bath for one hour. The precipitate was separated by filtration to give an ulipristal acetate isopropanol hemisolvate wet crystal (1.782 g). The wet crystal (1.782 g) was dissolved in 17.8 mL of a mixed solvent containing ethanol and water [ethanol/water (volume ratio)=80/20] by heating, and the solution was allowed to cool to a room temperature taking about one hour and stirred at a room temperature for 17 hours. The resulting precipitate was separated by filtration and dried for 19 hours at a temperature of 100° C. under a reduced pressure of not more than 15 hPa to give 1.0 g of a crystal C (crystalline polymorphic form C). The X-ray powder diffraction spectrum of the crystalline polymorphic form C is shown in FIG. 1, and the differential scanning calorimetry spectrum thereof is shown in FIG. 2. Moreover, the diffraction peak intensity and relative intensity in each diffraction angle (grid interval d value) of the crystalline polymorphic form C are shown in Table 1.

TABLE 1

| Peak number | 2θ | Peak search setting width | d value | Intensity | Relative intensity |
|---|---|---|---|---|---|
| 1 | 9.000 | 0.176 | 9.8176 | 496545 | 87 |
| 2 | 9.290 | 0.129 | 9.5118 | 573438 | 100 |
| 3 | 9.660 | 0.141 | 9.1483 | 32155 | 6 |
| 4 | 10.760 | 0.141 | 8.2154 | 184379 | 33 |
| 5 | 11.460 | 0.129 | 7.7151 | 27227 | 5 |
| 6 | 12.230 | 0.153 | 7.2310 | 52258 | 10 |
| 7 | 13.070 | 0.153 | 6.7681 | 34832 | 7 |
| 8 | 13.960 | 0.118 | 6.3386 | 31827 | 6 |
| 9 | 14.270 | 0.129 | 6.2016 | 143850 | 26 |
| 10 | 15.550 | 0.129 | 5.6938 | 140981 | 25 |
| 11 | 15.730 | 0.106 | 5.6291 | 207082 | 37 |
| 12 | 15.870 | 0.106 | 5.5797 | 180768 | 32 |
| 13 | 16.640 | 0.153 | 5.3232 | 199796 | 35 |
| 14 | 17.640 | 0.153 | 5.0237 | 134958 | 24 |
| 15 | 17.910 | 0.176 | 4.9485 | 190161 | 34 |
| 16 | 18.310 | 0.165 | 4.8413 | 48306 | 9 |

TABLE 1-continued

| Peak number | 2θ | Peak search setting width | d value | Intensity | Relative intensity |
|---|---|---|---|---|---|
| 17 | 18.920 | 0.153 | 4.6866 | 134054 | 24 |
| 18 | 19.340 | 0.153 | 4.5857 | 116322 | 21 |
| 19 | 20.000 | 0.129 | 4.4359 | 23063 | 5 |
| 20 | 20.940 | 0.165 | 4.2388 | 23052 | 5 |
| 21 | 22.840 | 0.141 | 3.8903 | 41340 | 8 |
| 22 | 23.290 | 0.129 | 3.8162 | 21740 | 4 |
| 23 | 23.840 | 0.165 | 3.7293 | 78463 | 14 |
| 24 | 24.100 | 0.071 | 3.8897 | 21189 | 4 |
| 25 | 24.300 | 0.118 | 3.6598 | 29305 | 6 |
| 26 | 24.880 | 0.153 | 3.5744 | 48228 | 9 |
| 27 | 25.540 | 0.141 | 3.4848 | 39081 | 7 |
| 28 | 25.680 | 0.106 | 3.4662 | 20439 | 4 |
| 29 | 27.260 | 0.176 | 3.2687 | 35190 | 7 |
| 30 | 27.490 | 0.118 | 3.2419 | 28642 | 5 |

Example 2

The ulipristal acetate crystal (0.1 g) obtained in Comparative Example and the crystal C (0.1 g) obtained in Example 1 were mixed to give an ulipristal acetate substance. The X-ray powder diffraction spectrum of the crystalline polymorphic form A is shown in FIG. 3, and the differential scanning calorimetry spectrum thereof is shown in FIG. 4. Moreover, the diffraction peak intensity and relative intensity in each diffraction angle (grid interval d value) of the crystalline polymorphic form A are shown in Table 2.

TABLE 2

| Peak number | 2θ | Peak search setting width | d value | Intensity | Relative intensity |
|---|---|---|---|---|---|
| 1 | 8.950 | 0.059 | 9.8723 | 117262 | 13 |
| 2 | 9.200 | 0.153 | 9.6046 | 909978 | 100 |
| 3 | 11.420 | 0.129 | 7.7420 | 111952 | 13 |
| 4 | 11.700 | 0.118 | 7.5574 | 138598 | 16 |
| 5 | 12.000 | 0.153 | 7.3691 | 64339 | 8 |
| 6 | 14.570 | 0.153 | 6.0745 | 32458 | 4 |
| 7 | 15.230 | 0.141 | 5.8127 | 445131 | 49 |
| 8 | 15.730 | 0.059 | 5.6291 | 29270 | 4 |
| 9 | 15.920 | 0.141 | 5.5623 | 99980 | 11 |
| 10 | 16.530 | 0.176 | 5.3584 | 97384 | 11 |
| 11 | 17.020 | 0.106 | 5.2052 | 212875 | 24 |
| 12 | 17.210 | 0.106 | 5.1482 | 127643 | 15 |
| 13 | 17.410 | 0.141 | 5.0895 | 151743 | 17 |
| 14 | 17.610 | 0.141 | 5.0321 | 54979 | 7 |
| 15 | 18.070 | 0.118 | 4.9051 | 63909 | 8 |
| 16 | 18.340 | 0.129 | 4.8335 | 56374 | 7 |
| 17 | 19.070 | 0.165 | 4.6500 | 150154 | 17 |
| 18 | 20.470 | 0.118 | 4.3351 | 62815 | 7 |
| 19 | 22.910 | 0.094 | 3.8786 | 19100 | 3 |
| 20 | 23.650 | 0.071 | 3.7589 | 84081 | 10 |
| 21 | 23.890 | 0.118 | 3.7217 | 55242 | 7 |
| 22 | 24.140 | 0.071 | 3.6837 | 17902 | 2 |
| 23 | 24.350 | 0.118 | 3.6524 | 220346 | 25 |
| 24 | 24.780 | 0.071 | 3.5900 | 46366 | 6 |
| 25 | 26.530 | 0.141 | 3.3570 | 22271 | 3 |
| 26 | 27.650 | 0.141 | 3.2235 | 35719 | 4 |
| 27 | 32.650 | 0.165 | 2.7404 | 24996 | 3 |
| 28 | 33.430 | 0.082 | 2.6782 | 18411 | 3 |
| 29 | 34.940 | 0.082 | 2.5658 | 35439 | 4 |
| 30 | 35.030 | 0.059 | 2.5595 | 19308 | 3 |

Example 3

The ulipristal acetate crystal (1.3 g) obtained in Comparative Example was dissolved in 6.5 mL of ethanol by heating. The solution was allowed to stand at 26° C. for one hour and then at 4° C. for 16 hours. The resulting precipitate was separated by filtration and dried under a reduced pressure until the weight reached a constant value, and 1.0 g of a crystal B was obtained. The crystal B (0.1 g) and the crystal C (0.1 g) obtained in Example 1 were mixed to give an ulipristal acetate substance. The X-ray powder diffraction spectrum of the crystalline polymorphic form B is shown in FIG. 5, and the differential scanning calorimetry spectrum thereof is shown in FIG. 6. Moreover, the diffraction peak intensity and relative intensity in each diffraction angle (grid interval d value) of the crystalline polymorphic form B are shown in Table 3.

TABLE 3

| Peak number | 2θ | Peak search setting width | d value | Intensity | Relative intensity |
|---|---|---|---|---|---|
| 1 | 6.410 | 0.153 | 13.7775 | 123754 | 37 |
| 2 | 8.410 | 0.082 | 10.5050 | 208444 | 62 |
| 3 | 8.990 | 0.071 | 9.8285 | 50955 | 16 |
| 4 | 9.160 | 0.059 | 9.6465 | 99364 | 30 |
| 5 | 9.350 | 0.141 | 9.4509 | 294241 | 87 |
| 6 | 9.640 | 0.153 | 9.1672 | 311885 | 93 |
| 7 | 11.790 | 0.141 | 7.4999 | 97918 | 29 |
| 8 | 12.750 | 0.165 | 6.9373 | 157752 | 47 |
| 9 | 13.360 | 0.071 | 6.6219 | 41904 | 13 |
| 10 | 13.460 | 0.106 | 6.5729 | 38720 | 12 |
| 11 | 14.450 | 0.082 | 6.1247 | 101060 | 30 |
| 12 | 14.530 | 0.094 | 6.0912 | 95603 | 29 |
| 13 | 15.260 | 0.129 | 5.8014 | 126572 | 38 |
| 14 | 15.700 | 0.106 | 5.6398 | 34881 | 11 |
| 15 | 16.720 | 0.188 | 5.2979 | 180337 | 54 |
| 16 | 17.280 | 0.129 | 5.1275 | 146882 | 44 |
| 17 | 17.470 | 0.106 | 5.0722 | 338814 | 100 |
| 18 | 17.880 | 0.153 | 4.9568 | 31182 | 10 |
| 19 | 18.590 | 0.153 | 4.7690 | 284305 | 84 |
| 20 | 18.730 | 0.059 | 4.7337 | 69226 | 21 |
| 21 | 18.920 | 0.082 | 4.6866 | 59328 | 18 |
| 22 | 19.340 | 0.153 | 4.5857 | 72477 | 22 |
| 23 | 20.970 | 0.176 | 4.2328 | 126309 | 38 |
| 24 | 21.320 | 0.118 | 4.1641 | 34931 | 11 |
| 25 | 21.490 | 0.176 | 4.1316 | 44872 | 14 |
| 26 | 22.240 | 0.141 | 3.9939 | 30974 | 10 |
| 27 | 24.130 | 0.129 | 3.6852 | 45421 | 14 |
| 28 | 25.530 | 0.165 | 3.4862 | 81415 | 25 |
| 29 | 26.970 | 0.082 | 3.3032 | 28409 | 9 |
| 30 | 28.210 | 0.094 | 3.1608 | 37295 | 11 |

The results of Comparative Example and Examples are shown in Tables 4 and 5.

TABLE 4

| | Comparative Example | Example 1 | Example 2 | Example 3 |
|---|---|---|---|---|
| Solubility (μg/mL) | 6.4 | 11.2 | 10.0 | 9.5 |

As apparent from Table 4, Examples 1 to 3 show significantly high solubility and excellent bioavailability compared with Comparative Example.

TABLE 5

| Pharmacokinetic parameters | Comparative Example | Example 1 |
|---|---|---|
| $T_{1/2}$ (hr) | 14.9 | 37.3 |
| $T_{max}$ (hr) | 1.8 | 1.2 |
| $C_{max}$ (ng/mL) | 1490.7 | 2200.2 |
| $AUC_{0-t}$ (ng · hr/mL) | 8447.4 | 12194.3 |
| $AUC_{0-inf}$ (ng · hr/mL) | 9390.7 | 18078.4 |

TABLE 5-continued

| Pharmacokinetic parameters | Comparative Example | Example 1 |
|---|---|---|
| $MRT_{last}$ (hr) | 11.8 | 11.7 |
| $MRT_{inf}$ (hr) | 16.6 | 37.7 |

As apparent from Table 5, Example 1 is excellent in the respects of all of $T_{max}$, $C_{max}$, $AUC_{0-t}$, $AUC_{0-inf}$ and $MRT_{last}$, compared with Comparative Example and shows excellent pharmacokinetics as a pharmaceutical product which is quickly be absorbed into the body.

Preparation Example 1

A capsule was obtained by filling the crystal C obtained in Example 1 into a capsule shell (Size 0).

Preparation Example 2

The crystal C obtained in Example 1 and carrier components were mixed in accordance with the following formulation. The mixture was granulated by dry granulating and then sized to give a granule.

[Formulation]

| | |
|---|---|
| Crystal C obtained in Example 1 | 300 mg |
| Crystalline cellulose | 590 mg |
| Sodium carboxymethyl starch | 50 mg |
| Glycerin fatty acid ester | 50 mg |
| Talc | 10 mg |
| Total amount | 1000 mg |

Preparation Example 3

The granule obtained in Preparation Example 2 and carrier components were mixed in accordance with the following formulation. The mixture was subjected to tablet compression to give a tablet.

[Formulation]

| | |
|---|---|
| Granule obtained in Preparation Example 2 | 100 mg |
| Crystalline cellulose | 174 mg |
| Glycerin fatty acid ester | 20 mg |
| Talc | 4 mg |
| Light silicic anhydride | 2 mg |
| Total amount | 300 mg |

Preparation Example 4

The tablet obtained in Preparation Example 3 was coated with a coating agent having the following formulation to give a film-coated tablet.

[Formulation of coating agent]

| | |
|---|---|
| Hypromellose | 70.5% by weight |
| Titanium oxide | 20.5% by weight |
| Propylene glycol | 6.9% by weight |
| Iron sesquioxide | 2.1% by weight |

INDUSTRIAL APPLICABILITY

The crystalline polymorphic form of the ulipristal acetate or the ulipristal acetate substance according to the present invention has an extremely high solubility and more excellent stability or absorption compared with a conventional crystalline form, and can improve bioavailability. Therefore, the crystalline polymorphic form or the ulipristal acetate substance of the present invention is preferably used as a selective progesterone receptor modulator. Moreover, the crystalline polymorphic form or the ulipristal acetate substance of the present invention is useful for prevention and/or treatment of a gynecological disease [for example, uterine leiomyoma or a disease attributable to uterine leiomyoma (e.g., metastatic leiomyoma, dysmenorrhea, menorrhagia, anemia, infertility, constipation, pollakiuria, and lumbago)]. Further, the crystalline polymorphic form or the ulipristal acetate substance of the present invention is also useful as an emergency contraceptive agent.

The invention claimed is:

1. A crystalline polymorphic form C of ulipristal acetate having an X-ray powder diffraction pattern comprising diffraction peaks at the following diffraction 2theta angles: 9.0±0.2°, 9.3±0.2°, 10.8±0.2°, 11.5±0.2°, 12.2±0.2°, 13.1±0.2°, 14.3±0.2°, 15.6±0.2°, 15.7±0.2°, 15.9±0.2°, 16.6±0.2°, 17.6±0.2°, 17.9±0.2°, 18.9±0.2°, 19.3±0.2°, and 23.8±0.2; wherein the crystalline polymorphic form C of ulipristal acetate has a differential scanning calorimetry spectrum comprising an endothermic peak at about 135 to 145° C.

2. A ulipristal acetate substance comprising the crystalline polymorphic form C of ulipristal acetate recited in claim 1.

3. The ulipristal acetate substance according to claim 2, which further comprises a crystalline polymorphic form A of ulipristal acetate, wherein the crystalline polymorphic form A has an X-ray powder diffraction pattern comprising diffraction peaks at the following diffraction 2theta angles: 9.2±0.2°, 11.4±0.2°, 11.7±0.2°, 12.0±0.2°, 15.2±0.2°, 17.0±0.2°, 17.2±0.2°, 24.4±0.2°.

4. The ulipristal acetate substance according to claim 3, wherein the ratio of the crystalline polymorphic form C relative to the crystalline polymorphic form A is 0.5/99.5 to 99.5/0.5 in a weight ratio of the former/the latter.

5. The ulipristal acetate substance according to claim 2, which further contains a crystalline polymorphic form B of ulipristal acetate, wherein the crystalline polymorphic form B has an X-ray powder diffraction pattern comprising diffraction peaks at the following diffraction 2theta angles: 6.4±0.2°, 8.4±0.2°, 9.4±0.2°, 9.6±0.2°, 11.8±0.2°, 12.8±0.2°, 15.3±0.2°, 16.7±0.2°, 17.5±0.2°, 18.6±0.2°, 19.3±0.2°, 21.0±0.2°, 25.5±0.2°.

6. The ulipristal acetate substance according to claim 5, wherein the ratio of the crystalline polymorphic form C relative to the crystalline polymorphic form 13 is 0.5/99.5 to 99.5/0.5 in a weight ratio of the former/the latter.

7. A pharmaceutical composition comprising the crystalline polymorphic form C of ulipristal acetate recited in claim 1 or the ulipristal acetate substance recited in claim 2, and a pharmaceutically acceptable excipient.

8. A process for producing the crystalline polymorphic form C of ulipristal acetate of claim 1, comprising:
(a) providing an isopropanol-solvated crystal of ulipristal acetate;
(b) dissolving the isopropanol-solvated crystal of ulipristal acetate by heating in a mixed solvent containing ethanol and water at a volume ratio of about 75/25 to about 85/15, wherein the amount of the isopropanol-solvated crystal of ulipristal acetate in the mixed solvent is 1 g of the crystal in about 5 to 15 ml of the mixed solvent;

(c) cooling the solution from step (b) to room temperature with a cooling rate ranging from 0.05 to 3° C./minute and stirring the solution at room temperature;

(d) recovering ulipristal acetate product formed in step (c) and drying the ulipristal acetate product under a reduced pressure, at a temperature ranging from 80° C. to 110° C., for 5 to 24 hours; and (e) recovering crystalline polymorphic form C of ulipristal acetate.

9. The process according to claim 8, carried out without addition of a seed crystal to the solution.

10. A method for providing contraception or for treating uterine fibroids in a woman in need thereof, comprising administering an effective amount of the crystalline polymorphic form C of ulipristal acetate recited in claim 1 or the ulipristal acetate substance recited in claim 2.

* * * * *